(12) United States Patent
Komoriya et al.

(10) Patent No.: US 6,858,760 B2
(45) Date of Patent: Feb. 22, 2005

(54) FLUORINE-CONTAINING CYCLIC COMPOUNDS, FLUORINE-CONTAINING POLYMERIZABLE MONOMERS, FLUORINE-CONTAINING POLYMERS RESIST COMPOSITIONS AND PATTERNING METHOD

(75) Inventors: Haruhiko Komoriya, Saitama (JP);
Satoru Miyazawa, Saitama (JP);
Katsunori Kawamura, Saitama (JP);
Satoru Kobayashi, Saitama (JP);
Kazuhiko Maeda, Tokyo (JP)

(73) Assignee: Central Glass Company, Limited, Ube (JP)

( * ) Notice: Subject to any disclaimer, the term of this patent is extended or adjusted under 35 U.S.C. 154(b) by 0 days.

(21) Appl. No.: 10/781,844

(22) Filed: Feb. 20, 2004

(65) Prior Publication Data

US 2004/0225159 A1 Nov. 11, 2004

(30) Foreign Application Priority Data

Feb. 21, 2003 (JP) ........................................ 2003-043496
May 14, 2003 (JP) ........................................ 2003-135228

(51) Int. Cl.⁷ ............................................. C07C 35/22
(52) U.S. Cl. .................... 568/820; 430/270.1; 430/322; 430/326; 430/907; 526/245; 526/247; 560/220; 568/667; 568/669
(58) Field of Search ................................ 568/820, 667, 568/669; 560/220; 526/245, 247; 430/270.1, 322, 326, 907

(56) References Cited

U.S. PATENT DOCUMENTS 6,794,110 B2 * 9/2004 Breyta et al. ............. 430/270.1

2004/0053161 A1 * 3/2004 Kanna et al ............. 430/270.1
2004/0091813 A1 * 5/2004 Poss et al. ............... 430/270.1
2004/0175645 A1 * 9/2004 Sasaki et al. ............. 430/270.1

OTHER PUBLICATIONS

Theodore H. Fedynshyn et al., "Fluoroaromatic Resists for 157–nm Lithography", Journal of Photopolymer Science and Technology, 2002, pp. 655–666, vol. 15, No. 4.

Ralph R. Dammel et al., "New Resin Systems for 157 nm Lithography", Journal of Photopolymer Science and Technology, 2001, pp. 603–612, vol. 14, No. 4.

* cited by examiner

Primary Examiner—Michael L. Shippen
(74) Attorney, Agent, or Firm—Crowell & Moring LLP

(57) ABSTRACT

A fluorine-containing cyclic compound is represented by the formula 1:

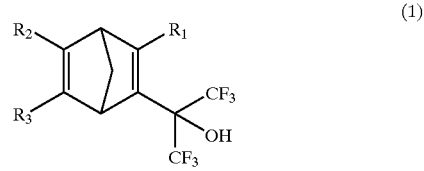

(1)

wherein each of $R_1$, $R_2$ and $R_3$ independently represents a hydrogen, alkyl group, fluorine, fluoroalkyl group or hexafluorocarbinol group, wherein at least one of the hexafluorocarbinol groups may partly or totally be protected with a protecting group, and wherein the protecting group is (a) a straight-chain, branched or cyclic hydrocarbon group having a carbon atom number of 1–25 or (b) an aromatic hydrocarbon group and optionally contains a fluorine atom, oxygen atom, nitrogen atom or carbonyl bond.

15 Claims, No Drawings

FLUORINE-CONTAINING CYCLIC COMPOUNDS, FLUORINE-CONTAINING POLYMERIZABLE MONOMERS, FLUORINE-CONTAINING POLYMERS RESIST COMPOSITIONS AND PATTERNING METHOD

BACKGROUND OF THE INVENTION

The present invention relates to novel, fluorine-containing cyclic compounds, fluorine-containing polymers prepared by polymerization or copolymerization of such compounds, and particularly to resist compositions used for vacuum ultraviolet wavelength region and patterning methods for making resist patterns.

Fluorine-containing compounds have been used or developed in various fields particularly in the field of advanced materials due to their good qualities (e.g., water repellency, oil repellency, low water absorption, heat resistance, weather resistance, corrosion resistance, transparency, photosensitivity, low refractive index, and low dielectric property). In particular, they are used in the coating field in view of their characteristic transparency behavior in each wavelength. Recently, there have been active researches and developments of (a) anti-reflection films taking advantage of their low refractive indexes and visible light transparency, (b) optical devices taking advantage of their transparency in long wavelength band (optical communication wavelength band), and (c) resist compositions taking advantage of their transparency in ultraviolet region (particularly vacuum ultraviolet region). A common aim in polymer design of such researches and developments is to achieve good adhesion to substrate and high glass transition point hardness), while achieving transparency in each wavelength for use by introducing as many fluorine atoms as possible. There are various proposals of increasing transparency at each wavelength by increasing the fluorine content in material design. However, there are few reports on improving fluorine-containing monomers themselves in hydrophilicity and adhesion and on obtaining high glass transition point.

Recently, in next generation $F_2$ resist field of vacuum ultraviolet region, there were reports on a hydroxyl-containing fluorostyrene (see T. H. Fedynyshyn, A. Cabral et al., J. Photopolym. Sci. Technol., 15, 655–666 (2002)) and on a hydroxyl-containing fluoronorbornene compound (see Ralph R. Dammel, Raj Sakamuri et al., J. Photopolym. Sci. Technol., 14, 603–611 (2001)). Thus, there was emerged an idea of containing fluorine and making polarity of hydroxyl group coexistent in the molecule. However, compatibility between transparency in ultraviolet region and etching resistance is still insufficient, and there exist many factors to be improved. Furthermore, conventional fluorine containing norbornene compounds have an electron attracting group (e.g., fluorine atom and trifluoromethyl group) directly bonded to norbornene ring, thereby lowering electron density of a polymerizable double bond. Thus, there are problems of low yield and insufficient molecular weight in synthesis of the target polymers from the above norbornene compounds. Thus, conventional compounds are not necessarily sufficient in capability, and there has been a demand for creating novel monomers or raw materials capable of efficiently providing further improved polymers, which are free of the above-mentioned defects.

SUMMARY OF THE INVENTION

It is therefore an object of the present invention to provide a novel fluorine-containing cyclic compound or fluorine-containing polymerizable monomer, which is capable of providing a fluorine-containing polymer that is high in transparency in a wide wavelength region from ultraviolet region to near infrared region.

It is another object of the present invention to provide the fluorine-containing polymer prepared by a polymerization or copolymerization using the fluorine-containing polymerizable monomer.

It is a further object of the present invention to provide a resist composition by using the fluorine-containing polymer so that the resist composition is improved in adhesion to substrate and film-forming property.

It is a still further object of the present invention to provide a process for making a resist pattern by using the resist composition.

According to the present invention, there is provided a fluorine containing cyclic compound represented by the formula 1:

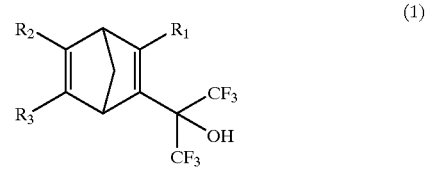

(1)

wherein each of $R_1$, $R_2$ and $R_3$ independently represents a hydrogen, alkyl group, fluorine, fluoroalkyl group or hexafluorocarbinol group, wherein at least one of the hexafluorocarbinol groups may partly or totally be protected with a protecting group, and wherein the protecting group is (a) a straight-chain, branched or cyclic hydrocarbon group having a carbon atom number of 1–25 or (b) an aromatic hydrocarbon group and optionally contains a fluorine atom, oxygen atom, nitrogen atom or carbonyl bond.

According to the present invention, there is provided a fluorine-containing cyclic compound (derived from the above fluorine-containing cyclic compound) represented by the formula 4 or 5:

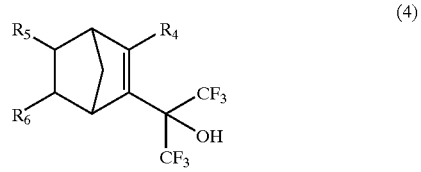

(4)

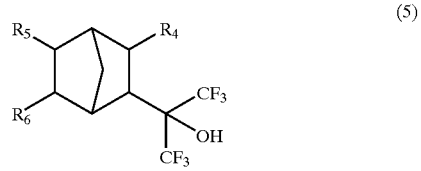

(5)

wherein at least one of $R_4$, $R_5$ and $R_6$ represents a hydroxyl group, and the remaining group of $R_4$, $R_5$ and $R_6$ other than the hydroxyl group represents a hydrogen, alkyl group, fluorine, fluoroalkyl group, or hexafluorocarbinol group, wherein at least one of the hexafluorocarbinol groups of the formula 4 or 5 may partly or totally be protected with a protecting group, and wherein the protecting group is (a) a straight-chain, branched or cyclic hydrocarbon group having a carbon atom number of 1–25 or (b) an aromatic hydrocarbon group and optionally contains a fluorine atom, oxygen atom, nitrogen atom or carbonyl bond.

According to the present invention, there is provided a resist composition comprising the fluorine-containing polymer.

According to the present invention, there is provided a process for making a resist pattern. This process comprises the sequential steps of.

(a) applying the resist composition to a supporting member to form a photosensitive layer on the supporting member;

(b) exposing the photosensitive layer to a light through a masking pattern to form a first precursory layer;

(c) heating the first precursory layer into a second precursory layer; and (d) developing the second precursory layer into the resist pattern.

DESCRIPTION OF THE PREFERRED EMBODIMENTS

The novel fluorine-containing cyclic compound according to the present invention, which contains a hexafluorocarbinol group on a norbornene or norbornadiene ring, contains a polar group in the molecule while its fluorine content is high. With this, the polymer prepared by a polymerization or copolymerization of the fluorine-containing cyclic compound becomes high in transparency in a wide wavelength region from ultraviolet region to near infrared region and becomes improved in adhesion to substrate and film-forming property. Furthermore, the resulting resist compositions are high in etching resistance due to their alicyclic structure. It is possible to make a resist pattern by the above process.

As stated above, a fluorine-containing cyclic compound according to the present invention is represented by the following formula 1.

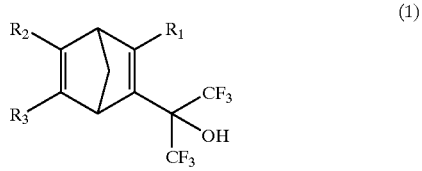

(1)

In this compound, at least one hexafluorocarbinol group is bonded to a norbornadiene optionally having a substituent(s) (i.e., $R_1$, $R_2$ and $R_3$).

In general, as the fluorine content is increased in fluorine-containing compounds, it known that transparency is improved in a wide wavelength range from ultraviolet region to near infrared region and that refractive index is lowered. On the other hand, as the fluorine content is increased, adhesion to substrate is lowered, and film-forming property becomes inferior. According to the compound of the formula 1, however, it is possible to contain fluorine atoms and a hydroxyl group(s) in the same molecule due to its hexafluorocarbinol group(s). Therefore, polymers derived from the compound of the formula 1 are provided with improved adhesion to substrate and improved film forming property. Furthermore, the norbornadiene skeleton of the formula 1 contributes to etching resistance of resist materials.

As stated above) each of $R_1$, $R_2$ and $R_3$ independently represents a hydrogen, alkyl group, fluorine, fluoroalkyl group or hexafluorocarbinol group. Each of the alkyl and fluoroalkyl groups preferably has a carbon atom number of 1–5, since the degree of polymerization may be lowered by steric hindrance as the carbon atom number increases, since transparency is lowered, and since refractive index increases. Examples of the alkyl group include methyl group, ethyl group, n-propyl group, isopropyl group, n-butyl group, sec-butyl group, and tertbutyl group. Hydrogen atoms of the alkyl group way be partially or totally replaced with fluorine atoms. It is preferable to use a hexafluorocarbinol group due to its high content of fluorine.

At least one of the hexafluorocarbinol groups contained in the formula 1 may partly or totally be protected with a protecting group. The protecting group is (a) a straight-chain, branched or cyclic hydrocarbon group having a carbon atom number of 1–25 or (b) an aromatic hydrocarbon group. The protecting group optionally contains a fluorine atom, oxygen atom, nitrogen atom or carbonyl bond. Examples of the protecting group include methyl group, ethyl group, n-propyl group, isopropyl group, cyclopropyl group, sec butyl group, tert-butyl group, n-pentyl group, cyclopentyl group, sec-pentyl group, neopentyl group, hexyl group, cyclohexyl group, norbornel group, adamantyl group, vinyl group, allyl group, butenyl group, pentenyl group, ethynyl group, phenyl group, benzyl group, and 4-methoxybenzyl group.

Examples of the protecting group containing oxygen atom include alkoxycarbonyl group, acetal group, and acyl group. Examples of the alkoxycarbonyl group are tert-butoxycarbonyl group, tert-amyloxycarbonyl group, methoxycarbonyl group, ethoxycarbonyl group, and i-propoxycarbonyl group. Examples of the acetal group include (a) those of acyclic ethers, such as methoxymethyl group, methoxyethoxymethyl group, ethoxyethyl group, butoxyethyl group, cyclohexyloxyethyl group, benzyloxyethyl group, phenethyloxyethyl group, ethoxypropyl group, benzyloxypropyl group, phenethyloxypropyl group, ethoxybutyl group, and ethoxyisobutyl group, and (b) those of cyclic ethers, such as tetrahydrofuranyl group and tetrahydropyranyl group. Examples of the acyl group include acetyl group, propionyl group, butyryl group, heptanoyl group, hexanoyl group, valeryl group, pivaloyl group, isovaleryl group, lauryloyl group, myristoyl group, palmiotyl group, stearoyl group, oxalyl group, malonyl group, succinyl group, glutaryl group, adipoyl group, piperoyl group, suberoyl group, azelaoyl group, sebacoyl group, acryloyl group, propioloyl group, methacryloyl group, crotonoyl group, oleoyl group, maleoyl group, fumaroyl group, mesaconoyl group, campholoyl group, benzyl group, phthaloyl group, isophthaloyl group, terephthaloyl group, naphthoyl group, toluoyl group, hydratoropoyl group, atoropoyl group, cinnamoyl group, furoyl group, thenoyl group, nicotinoyl group, and isonicotinoyl group. Furthermore, these exemplary groups as the protecting groups may be ones in which hydrogen atoms have been partially or fully replaced with fluorine atoms.

The compound represented by the following formula 4 or 5 according to the present invention is a fluorine-containing cyclic compound containing at least one hydroxyl group. These compounds can be derived from the fluorine-containing cyclic compound of the formula 1.

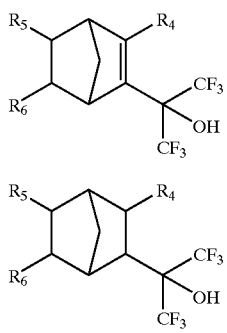

(4)

(5)

Similar to the compound 1, these compounds 4 and 5 have many fluorine atoms in the molecule and at the same time have at least one hexafluorocarbinol group in the molecule. Thus, these compounds can provide a good transparency in wide wavelength range and a superior adhesion to substrate. The norbornene or norbornane skeleton contributes to etching resistance that is required for resist compositions. In each of the formulas 4 and 5, at least one of $R_4$, $R_5$ and $R_6$ represents a hydroxyl group. This hydroxyl group is capable of acting as a site for introducing a polymerizable group. The remaining group(s) of $R_4$, $R_5$ and $R_6$ other than the hydroxyl group represents a hydrogen, alkyl group, fluorine, fluoroalkyl group, or hexafluorocarbinol group. Specific examples of the remaining group(s) may be the same as those of $R_1$, $R_2$ and $R_3$ of the formula 1. At least one of the hexafluorocarbinol groups of the formula 4 or 5 may partly or totally be protected with a protecting group. This protecting group is (a) a straight-chain, branched or cyclic hydrocarbon group having a carbon atom number of 125 or (b) an aromatic hydrocarbon group and optionally contains a fluorine atom, oxygen atom, nitrogen atom or carbonyl bond. Examples of this protecting group may be the same as those of the protecting group of the formula 1.

The compounds represented by the following formulas 10 and 11 according to the present invention are fluorine containing polymerizable monomers. These compounds can be derived from the fluorine-containing cyclic compounds 4 and 5.

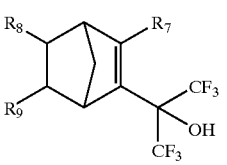

(10)

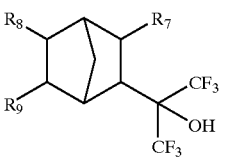

(11)

One of $R_7$, $R_8$ and $R_9$ in the formula 10 or 11 is a polymerizable group represented by the formula 12:

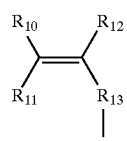

(12)

In the formula 12, each of $R_{10}$ to $R_{12}$ independently represents a hydrogen atom, fluorine atom, or a straight-chain, branched or cyclic alkyl or fluoroalkyl group having a carbon atom number of 1–25. $R_{13}$ represents a single bond (direct bond), a methylene group, a straight-chain, branched or cyclic fluoroalkylene group having a carbon atom number of 2–20, an oxygen atom, a sulfur atom, —(C=O)O—, or a dialkylsilylene group. Examples of the polymerizable group (represented by the formula 12) include vinyl group, allyl group, acryloyl group, methacryloyl group, fluorovinyl group, difluorovinyl group, trifluorovinyl group, difluorotrifluoromethylvinyl group, trifluoroallyl group, perfluoroallyl group, trifluoromethylacryloyl group, and nonafluorobutylacryloyl group. Of these, acryloyl group, methacryloyl group, and trifluoromethylacryloyl group are preferable, due to their high polymerizability and copolymerizability with other monomers. A fluorine-containing polymerizable group is used for providing transparency and low refractive index. The remaining group(s) of $R_7$, $R_8$ and $R_9$ other than the polymerizable group of the formulas 10 and 11 represents a hydrogen, alkyl group, fluorine, fluoroalkyl group, or hexafluorocarbinol group. Specific examples of the remaining group(s) may be the same as those of $R_1$, $R_2$ and $R_3$ of the formula 1. At least one of the hexafluorocarbinol groups of the formula 10 or 11 may partly or totally be protected with a protecting group. This protecting group is (a) a straight-chain, branched or cyclic hydrocarbon group having a carbon atom number of 1–20 or (b) an aromatic hydrocarbon group and optionally contains a fluorine atom, oxygen atom, nitrogen atom or carbonyl bond. Specific examples of this protecting group may be the same as those of the protecting group of the hexafluorocarbinol group of the formula 1.

An acid-labile protecting group usable in the present invention is not particularly limited, as long as it is a group that is released by the effect of photoacid generator or hydrolysis. Examples of the acid-labile protecting group include alkoxycarbonyl group, acetal group, and acyl group. Examples of the alkoxycarbonyl group include tert-butoxycarbonyl group, tert-amyloxycarbonyl group, methoxycarbonyl group, ethoxycarbonyl group, and i-propoxycarbonyl group. Examples of the acetal group include those of acyclic ethers, such as methoxymethyl group, methoxyethoxymethyl group, ethoxyethyl group, butoxyethyl group, cyclohexyloxyethyl group, benzyloxyethyl group, phenethyloxyethyl group, ethoxypropyl group, benzyloxypropyl group, phenethyloxypropyl group, ethoxybutyl group, and ethoxyisobutyl group. In case that $R_2$ and $R_3$ are hydrogen atoms, the acid-labile protecting group may be an acetal group prepared by adding a vinyl ether to the hydroxyl group. Examples of the silyl group are trimethylsilyl group, ethyldimethylsilyl group, methyldiethylsilyl group, triethylsilyl group, i-propyldimethylsilyl group, methyldi-i-propylsilyl group, tri-i-propylsilyl group, t-butyldimethylsilyl group, methyldi-t-butylsilyl group, tri-t-butylsilyl group, phenyldimethylsilyl group, methyldiphenylsilyl group, and triphenylsilyl group. Examples of the acyl group include acetyl group, propionyl group, butyryl group, heptanoyl group, hexanoyl group, valeryl group, pivaloyl group, isovaleryl group, lauryloyl group, myristoyl group, palmitoyl group, stearoyl group, oxalyl group, malonyl group, succinyl group, glutaryl group, adipoyl group, piperoyl group, suberoyl group, azelaoyl group, sebacoyl group, acryloyl group, propioloyl group, methacryloyl group, crotonoyl group, oleoyl group, maleoyl group, fumaroyl group, mesaconoyl group, campholoyl group, benzoyl group, phthaloyl group, isophthaloyl group, terephthaloyl group, naphthoyl group, toluoyl group, hydratoropoyl group, atoropoyl group, cinnamoyl group, furoyl group, thenoyl group, nicotinoyl group, and isonicotinoyl group. Furthermore, these exemplary groups as the acid-labile protecting group may be ones in which hydrogen atoms have been partially or fully replaced with fluorine atoms.

The acid-labile protecting group is used in the invention for providing positive-type photosensitivity and achieving good solubility in an alkali aqueous solution after exposure to high-energy rays (e.g. far ultraviolet rays of 300 nm or less in wavelength, excimer laser, and X rays) or electron beam. Depending on the application field of the present invention, the acid-labile protecting group may contain a fluorine atom(s) for providing transparency Or a cyclic structure for providing etching resistance or high glass transition point.

Fluorine-containing cyclic compounds according to the present invention may be represented by the following formulas 2 and S.

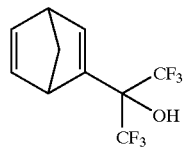
(2)

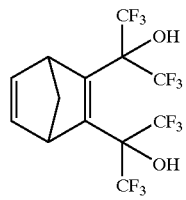
(3)

Furthermore, fluorine-containing cyclic compounds according to the present invention may be represented by the following formulas 6 to 9.

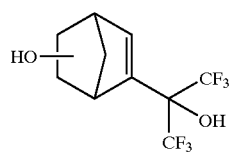
(6)

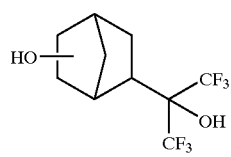
(7)

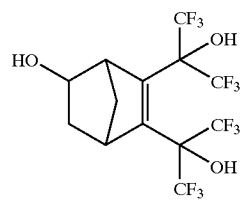
(8)

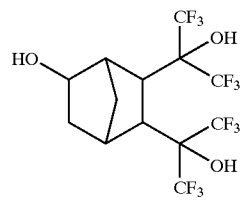
(9)

Still furthermore, fluorine-containing cyclic compounds according to the present invention may be represented by the following formulas 13 to 18:

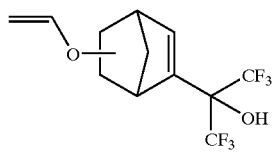
(13)

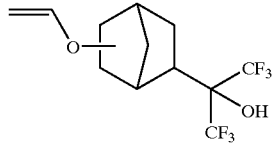
(14)

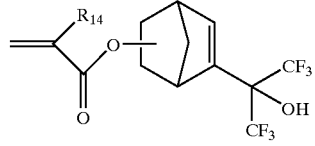
(15)

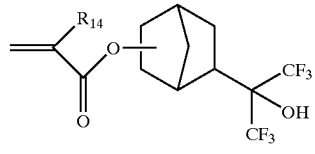
(16)

wherein $R_{14}$ of the formula 15 or 16 represents a hydrogen, methyl group or trifluoromethyl group,

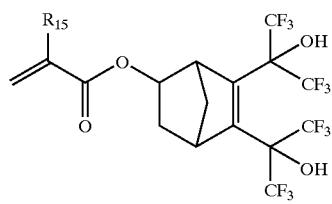
(17)

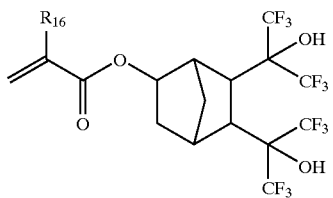

(18)

wherein $R_{15}$ of the formula 17 or 18 represents a hydrogen, methyl group or trifluoromethyl group.

Fluorine-containing polymers according to the present invention are those prepared by homopolymerization or copolymerization of the above-mentioned fluorine-containing cyclic compounds represented by the formulas 1 to 11 and 13 to 18.

Comonomers for producing the copolymers of the present invention are not particularly limited, as long as they have copolymerizability with the fluorine-containing cyclic compounds. Examples of such comonomers include maleic anhydride, acrylic esters, fluorine-containing acrylic esters, methacrylic esters, fluorine-containing methacrylic esters, styrene compounds, fluorine-containing styrene compounds, vinyl ethers, fluorine-containing vinyl ethers, allyl ethers, fluorine-containing allyl ethers, olefins, fluorine-containing olefins, norbornene compounds, fluorine-containing norbornene compounds, and sulfur dioxide.

Exemplary (meth)acrylic esters (i.e., acrylic esters and methacrylic esters) for the above-mentioned comonomer are not particularly limited with respect to their ester side chains. They are (meth)acrylic alkyl esters such as methyl (meth)acrylate, ethyl (meth)acrylate, n-propyl (meth)acrylate, isopropyl (meth)acrylate, n-butyl (meth)acrylate, isobutyl (meth)acrylate, n-hexyl (meth)acrylate, n-octyl (meth)acrylate, 2-ethylhexyl (meth)acrylate, lauryl (meth)acrylate, 2-hydroxyethyl (meth)acrylate, and 2-hydroxypropyl (meth)acrylate; (meth)acrylates containing groups such as ethylene glycol, propylene glycol and tetramethylene glycol; unsaturated amides such as (meth)acrylic amide, N-methylol(meth)acrylic amide, and diacetoneacrylic amide; (meth)acrylonitrile, alkoxysilane-containing vinyl silanes and (meth)acrylic esters, tert-butyl (meth)acrylate, and cyclic (meth)acrylate such as 3-oxocyclohexyl (meth)acrylate, adamantyl (meth)acrylate, alkyladamantyl (meth)acrylate, cyclohexyl (meth)acrylate, tricyclodecanyl (meth)acrylate and (meth)acrylate having cyclic structures such as lactone ring and norbornene ring; and (meth)acrylic acid. Further examples are (meth)acrylate containing a cyano group at α-position and analogous compounds such as maleic acid, fumaric acid and maleic anhydride.

The fluorine-containing (meth)acrylic esters for the above-mentioned comonomer may have a fluorine atom or fluorine-containing group at their α position or may have a substituent having a fluorine atom at ester moiety. Furthermore, it is also possible to use a fluorine-containing (meth)acrylic ester containing fluorine atoms at its α-position and ester moiety. It is optional to introduce a cyano group into the α-position. Such fluorine-containing groups at their α position may be trifluoromethyl group, trifluoroethyl group and nonafluoro-n-butyl group. When the fluorine-containing (meth)acrylic esters contain fluorine-containing groups at their α positions, fluorine may not be contained in the ester moieties. In case that α-trifluoromethylacrylic alkyl ester is used as a comonomer, it is possible to obtain polymers with a relatively high yield. Furthermore, the obtained polymers have good solubility in organic solvents.

Further exemplary fluorine-containing (meth)acrylic esters as the above-mentioned comonomer may have at their ester moiety a fluoroalkyl or perfluoroalkyl group or a fluorine-containing cyclic structure. This cyclic structure may have a substituent (e.g., fluorine atom, trifluoromethyl group, and hexafluorocarbinol group), and its examples are fluorine-containing benzene ring, fluorine-containing cyclopentane ring, fluorine-containing cyclohexane ring, and fluorine-containing cycloheptane ring. Further exemplary (meth)acrylic esters may have at their ester moiety a fluorine-containing t-butyl ester group. The fluorine-containing (meth)acrylic esters may have fluorine-containing alkyl groups at their α-positions, too. Specific examples of the fluorine-containing (meth)acrylic ester include 2,2,2-trifluoroethyl(meth)acrylate, 2,2,3,3-tetrafluoropropyl(meth)acrylate, 1,1,1,3,3,3-hexafluoroisopropyl(meth)acrylate, heptafluoroisopropyl (meth)acrylate, 1,1-dihydroheptafluoro-n-butyl(meth) acrylate, 1,1,5-trihydrooctafluoro-n-pentyl(meth)acrylate, 1,1,2,2-tetrahydrotridecafluoro-n-octyl(meth)acrylate, 1,1,2, 2-tetrahydroheptadecafluoro-n-decyl(meth)acrylate, perfluorocyclohexylmethyl(meth)acrylate, 6-[3,3,3-trifluoro-2-hydroxy-2-(trifluoromethyl)propyl]bicyclo [2.2.1]heptyl-2-yl(meth)acrylate, 6-[3,3,3-trifluoro-2-hydroxy-2-(trifluoromethyl)propyl]bicyclo[2.2.1]heptyl-2-yl-2(trifluoromethyl)(meth)acrylate, 1,4-bis(1,1,1,3,3,3-hexafluoro-2-hydroxyisopropyl)cyclohexyl(meth)acrylate, and 1,4-bis(1,1,1,3,3,3-hexafluoro-2-hydroxyisopropyl) cyclohexyl-2-trifluoromethyl(meth)acrylate.

Further examples of the above mentioned comonomer are styrene compounds and fluorine-containing styrene compounds, such as styrene, fluorinated styrene, hydroxystyrene, and a compound in which a hexafluorocarbinol group(s) or functional group(s) (obtained by modifying the hydroxyl group of hexafluorocarbinol group) is bonded to the benzene ring. In other words, the comonomer can preferably be selected from fluorine-containing styrene and hydroxystyrene, each containing fluorine atom or trifluoromethyl group substituted for hydrogen, styrene compounds containing a halogen, an alkyl group or a fluorine-containing alkyl group at their α-position, and perfluorovinyl-containing styrene compounds.

Still further examples of the above-mentioned comonomer are vinyl others, fluorine-containing vinyl ethers, allyl ethers, and fluorine-containing allyl ethers. For example, the comonomer may be an alkyl vinyl ether or alkyl allyl ether that optionally contains methyl group, ethyl group, propyl group, butyl group, or hydroxyl group (e.g., hydroxyethyl group and hydroxybutyl group) and that optionally contains fluorine substituted for a part or all of the hydrogen atoms. The comonomer may be a cyclic vinyl ether or allyl ether containing a cyclohexyl group or a hydrogen or carbonyl bond in its cyclic structure. Furthermore, the comonomer can be selected from vinyl esters, vinyl silanes, olefins, fluorine-containing olefins, norbornene compounds, fluorine-containing norbornene compounds, and other compounds containing polymerizable unsaturated bonds, without any particular limitation upon use.

Exemplary olefins for the above-mentioned comonomer are ethylene, propylene, isobutene, cyclopentene, and cyclohexene. Exemplary fluorine-containing olefins for that are vinyl fluoride, vinylidene fluoride, trifluoroethylene, chlorotrifluoroethylene, tetrafluoroethylene, hexafluoropropylene, and hexafluoroisobutene.

The abovementioned norbornene compounds and fluorine-containing norbornene compounds as examples of the comonomer may have a mononucleus or multinucleus structure. It is possible to prepare the norbornene compounds (e.g., 3-(5-bicyclo[2.2.1]heptene-2-yl)-1,1,1-trifluoro-2- (trifluoromethyl)-2-propanol) by a Diels-Alder addition reaction of unsaturated compounds (e.g., allyl alcohol, fluorine-containing allyl alcohol, homoallyl alcohol, fluorine-containing homoalcohol, acrylic acid, α-fluoroacrylic acid, methacrylic acid, all of the above-mentioned (meth)acrylic esters and fluorine-containing (meth)acrylic esters, 2-(benzoyloxy)pentafluoropropane, 2-(methoxyethoxymethyloxy)pentafluoropropene, 2-(tetrahydroxypyranyloxy)pentafluoropropene, 2-(benzoyloxy)trifluoroethylene, and 2-(methoxymethyloxy)trifluoroethylene) to dienes (e.g., cyclopentadiene and cyclohexadiene).

The above-mentioned comonomer may be a single monomer or a combination of at least two monomers. Upon the polymerization, the ratio of the fluorine-containing cyclic compound to the comonomer is not particularly limited. The amount of the former is preferably 10–100%, more preferably 30–100%. If it is less than 30%, the resulting polymer may become insufficient in transparency or film-forming property depending on the wavelength range for use.

The polymerization or copolymerization method for obtaining the target polymer (copolymer) is not particularly limited. For example, it is preferable to use radical polymerization or ionic polymerization. In some cases, it is also possible to use coordinated anionic polymerization, living anionic polymerization, cationic polymerization, ring-opening metathesis polymerization, or vinylene polymerization.

Particulars of the above-mentioned radical polymerization are as follows. The radical polymerization can be conducted by a known manner such as bulk polymerization, solution polymerization, suspension polymerization or emulsion polymerization by a batch-wise, half-continuous or continuous operation.

The radical polymerization initiator is not particularly limited. Its examples are azo compounds, peroxides and redox compounds. Of these, preferable ones are azobisbutyronitrile, t-butylperoxypivalate, di-t-butylperoxide, i-butyrylperoxide, lauroylperoxide, succinic acid peroxide, dicinnamylperoxide, di-n-propylperoxydicarbonate, t-butylperoxyallyl monocarbonate, benzoyl peroxide, hydrogen peroxide, and ammonium persulfate.

The reaction vessel for conducting the polymerization (copolymerization) is not particularly limited. It is optional to use a solvent for conducting the polymerization. The polymerization solvent is preferably one that does not interfere with the radical polymerization. Its typical examples are esters such as ethyl acetate and n-butyl acetate; ketones such as acetone and methyl isobutyl ketone; hydrocarbons such as toluene and cyclohexane; and alcohols such as methanol, isopropyl alcohol and ethylene glycol monomethyl ether. Furthermore, it can be selected from various other solvents such as water, ethers, cyclic ethers, fluorohydrocarbons, and aromatic solvents. It is optional to use a single solvent or a mixture of at least two solvents. Furthermore, it is possible to use a molecular weight adjusting agent, such as mercaptan, in the polymerization. The temperature for conducting the polymerization may be suitably adjusted depending on the type of radical polymerization initiator or radical polymerization initiating source. It is preferably 20–200° C. particularly preferably 30–140° C.

The abovementioned ring-opening metathesis polymerization may be conducted by a known manner using a transition metal catalyst (containing a transition metal selected from the groups 4 to 7 of the periodic table) in the presence of a cocatalyst.

The transition metal catalyst (polymerization catalyst) is not particularly limited. Its examples include titanium compounds, vanadium compounds, molybdenum compounds, and tungsten compounds. In particular, preferable examples include titanium (IV) chloride, vanadium (IV) chloride, vanadium trisacetylacetonato, vanadium bisacetylacetonatodichloride, molybdenum (VI) chloride, and tungsten (VI) chloride. The amount of the polymerization catalyst may be in a range of 0.001–10 mol %, preferably 0.01–1 mol %, based on the total mole numbers of the monomers used in the polymerization.

The cocatalyst for conducting the ring-opening metathesis polymerization may be an alkylaluminum or alkyltin. Its specific examples include trialkylaluminums (e.g., trimethylaluminum, triethylaluminum, tripropyaluminum, triisopropylaluminum, triisobutylaluminum, tri-2-methylbutylaluminum, tri-3-methylbutylaluminum, tri-2-methylpentylaluminum, tri-3-methylpentylaluminum, tri-4-methylpentylaluminum, tri-2-methylhexylaluminum, tri-S-methylhexylaluminum, sad trioctylaluminum), dialkylaluminum halides (e.g., methylaluminum chloride, diethylaluminum chloride, diisopropylaluminum chloride, and diisobutylaluminumchloride), monoalkylaluminum halides (methylaluminum dichloride, ethylaluminum dichloride, ethylaluminum diiodide, propylaluminum dichloride, isopropylaluminum dichloride, butylaluminum dichloride, and isobutylaluminum dichloride), alylaluminum sesquichlorides (e.g., methylaluminum sesquichloride, ethylaluminum sesquichloride, propylaluminum sesquichloride, and isobutylaluminum sesquichloride), tetra-n-butyltin, tetraphenyltin, and triphenylchlorotin. The amount of the cocatalyst may be 100 equivalents or less, preferably 30 equivalents or less, per equivalent of the transition metal catalyst.

The polymerization solvent for conducting the ring-opening metathesis polymerization is not particularly limited, as long as it does not interfere with the polymerization. Its typical examples include aromatic hydrocarbons (e.g., benzene, toluene, xylene, chlorobenzene, and dichlorobenzene), hydrocarbons (e.g., hexane, heptane, and cyclohexane), and halogenated hydrocarbons (e.g., carbon tetrachloride, chloroform, methylene chloride, and 1,2-dichloroethane). These solvents may be used alone or in combination. The reaction temperature for conducting the ring-opening metathesis polymerization may be in a range of −70° C. to +200° C., preferably −30° C. to +60° C.

The above-mentioned vinylene polymerization may be conducted by a known manner using a polymerization catalyst that is a transition metal catalyst (containing a transition metal selected from the groups 8 to 10 of the periodic table, such as iron, nickel, rhodium, palladium, and platinum) or another transition metal catalyst (containing a metal selected from the groups 4 to 6 of the periodic table, such as zirconium, titanium, vanadium, chromium, molybdenum, and tungsten) in the presence of a cocatalyst.

The polymerization catalyst for conducting the vinylene polymerization is not particularly limited. Its examples include transition metal compounds (of transition metals of the groups 8 to 10 of the periodic table) such as iron (II) chloride, iron (III) chloride, iron (II) bromide, iron (III) bromide, iron (II) acetate, nickel bromide, nickel chloride, dichlorohexylnickel acetate, nickel lactate, nickel oxide, nickel tetrafluoroborate, bis(allyl)nickel, bis (cyclopentadienyl)nickel, nickel (II)

hexafluoroacetylacetonatotetrahydrate, nickel (II) trifluoroacetylacetonatodihydrate, nickel (II) acetylacetonatotetrahydrate, rhodium (III) chloride, rhodium tris(triphenylphosphine)trichloride, palladium(II) bis(trifluoroacetate), palladium(II) bis(acetylacetonato), palladium(II) 2-ethylhexanoate, palladium(II) bromide, palladium(II) chloride, palladium(II) iodide, palladium(II) oxide, monoacetonitriletris(triphenylphosphine)palladium (II) tretrafluoroborate, tetrakis(acetonitrile)palladium(II) tetrafluoroborate, dichlorobis(acetonitrile)palladium(II), dichlorobis(triphenylphosphine)palladium(II), dichlorobis(benzonitrile)palladium(II), palladium acetylacetonato, palladium bis(acetonitrile)dichloride, palladium bis(dimethylsulfoxide)dichloride, and platinum bis(triethylphosphine)hydrobromide Furthermore, its examples include transition metal compounds (of transition metals of the groups 4 to 6 of the periodic table) such as vanadium (IV) chloride, vanadium trisacetylacetonato, vanadium bisacetylacetonatodichloride, trimethoxy(pentamethylcyclopentadienyl)titanium (IV), bis(cyclopentadienyl)titanium dichloride, and bis(cyclopentadienyl)zirconium dichloride. The amount of the polymerization catalyst may be 0.001 mol % to 10 mol %, preferably 0.01 mol % to 1 mol %, based on the total mol numbers of the monomers used in the polymerization.

The cocatalyst for conducting the vinylene polymerization may be an alkylaluminoxane or alkylaluminum. Its specific examples include methylaluminoxane MAO, trialkylaluminums (e.g., trimethylaluminum, triethylaluminum, tripropylaluminum, triisopropylaluminum, triisobutylaluminum, tri-2-methylbutylaluminum, tri-3-methylbutylaluminum, tri-2-methylpentylaluminum, tri-3-methylpentylaluminum, tri-3-methylhexylaluminum, tri-2-methylhexylaluminum, tri-3-methylhexylaluminum, and trioctylaluminum), dialkylaluminum halides (e.g., methylaluminum chloride, diethylaluminum chloride, diisopropylaluminum chloride, and diisobutylaluminumchloride), monoalkylaluminum halides (e.g., methylaluminum dichloride, ethylaluminum dichloride, ethylaluminum diiodide, propylaluminum dichloride, isopropylaluminum dichloride, butylaluminum dichloride, and isobutylaluminum dichloride), and alkylaluminum sesquichlorides (e.g., methylaluminum sesquichloride, ethylaluminum sesquichloride, propylaluminum sesquichloride, and isobutylaluminum sesquichloride). The amount of the cocatalyst may be 100 equivalents or less, preferably 30 equivalents or less, per equivalent of the transition metal catalyst. Methylaluminoxane as the cocatalyst may be in an amount of 50–500 equivalents per equivalent of the transition metal catalyst. Other alkylaluminums may be in an amount of 100 equivalents or less, preferably 30 equivalents or less, per equivalent of the transition metal catalyst.

The polymerization solvent for conducting the vinylene polymerization is not particularly limited, as long as it does not interfere with the polymerization. Its typical examples include aromatic hydrocarbons (e.g., benzene, toluene, xylene, chlorobenzene, and dichlorobenzene), hydrocarbons (e.g., hexane, heptane, and cyclohexane), halogenated hydrocarbons (e.g., carbon tetrachloride, chloroform, methylene chloride, and 1,2-dichloroethane), dimethylformamide, N-methylpyrolidone, and N-cyclohexylpyrolidone. These solvents may be used alone or in combination. The reaction temperature for conducting the vinylene polymerization may be in a range of $-70°$ C. to $+200°$ C., preferably $-40°$ C. to $+80°$ C.

After the polymerization, it is possible to remove the reaction medium (i.e., organic solvent or water) from the solution or dispersion of the target polymer by a known method. For example, it can be conducted by reprecipitation followed by filtration, or by heating under vacuum to distill the medium off.

The target polymer according to the present invention may have a number average molecular weight (Mn) of 1,000–100,000, preferably 3,000–50,000.

The polymer according to the present invention may be formed into a film by dissolving the polymer in a solvent to prepare a coating solution and then by applying the coating solution to a substrate. This solvent is not particularly limited as long as the polymer can be dissolved therein. Its examples are ketones such as acetone, methyl ethyl ketone, cyclohexanone, methyl isoamyl ketone and 2-heptanone; polyhydric alcohols such as ethylene glycol, ethylene glycol monoacetate, diethylene glycol, diethylene glycol monoacetate, propylene glycol, propylene glycol monoacetate, dipropylene glycol, and ethers (monomethyl ether, monoethyl ether, monopropyl ether, monobutyl ether and monophenyl ether) of dipropylene glycol monoacetate, and derivatives of polyhydric alcohols; cyclic ethers such as dioxane; esters such as methyl lactate, ethyl lactate, methyl acetate, ethyl acetate, butyl acetate, methyl pyruvate, ethyl pyruvate, methyl methoxypropionate, and ethyl ethoxypropionate; aromatic solvents such as xylene and toluene; and fluorine-containing solvents such as fleon, alternative fleon, perfluoro compounds, and hexafluoroisopropyl alcohol. Furthermore, it is possible to use a high-boiling-point, weak solvent (e.g., a terpene based petroleum naphtha solvent or paraffinic solvent) for the purpose of increasing coatability (applicability of the coating solution). The solvent for preparing the coating solution may be a single solvent or a mixture of at least two solvents.

A resist composition according to the present invention is (1) a first resist composition containing both of a polymer (according to or not according to the present invention) and a dissolution inhibitor of which solubility in alkali aqueous solution changes by the action of acid or (2) a second resist composition that is a polymer containing a dissolution inhibitor as a part of the structure of the polymer. In other words, a fluorine-containing compound of the present invention may serve as the dissolution inhibitor of the first resist composition, and the polymer of the present invention serves as the polymer of the second resist composition. It is particularly preferable to use the first or second resist composition for producing positive-type resist compositions. Such resist composition is preferably used, for example, for preparing semiconductors using a 248 nm KrF or 193 nm ArP excimer laser, a vacuum ultraviolet (typically 157 nm) $F_2$ laser, electron beam or X-ray. In fact, the dissolution inhibitor, of which solubility in alkali aqueous solution changes by the action of acid, is characterized in that at least one of hexafluorocarbinol groups is an acid-labile protecting group, This dissolution inhibitor is not further particularly limited in its structure. This acid-labile protecting group may be selected from the above-mentioned examples and is a functional group that is to be severed by acid. The above first or second resist composition is insoluble or very slightly soluble in alkali aqueous solution prior to the activating energy ray irradiation. The activating energy ray irradiation, however, generates an acid from the acid generator. Then, the polymer is hydrolyzed by this acid and thereby becomes soluble in alkali aqueous solution.

The above-mentioned acid generator for a resist composition is not particularly limited. It can be suitably selected from acid generators for chemically amplified resists. Examples of such acid generators are bissulfonyldiazomethanes, nitrobenzyl derivatives, onium salts, halogen-containing triazine compounds, cyano group-containing oximesulfonate compounds, and other oximsulfonate compounds. The acid generator may be used in the form of a single compound or a mixture of at least two compounds. The content of the acid generator in the resist composition may be 0.5–20 parts by weight, relative to 100 parts by weight of the polymer. If it is less than 0.5 parts by weight, the resist composition may become insufficient in image forming capability. If it is greater than 20 parts by weight, it may become difficult to prepare a uniform solution of the resist composition. Thus, the resulting solution may become inferior in storage stability.

The above-mentioned resist composition according to the present invention can be used in conventional resist patterning methods, as exemplified in the following. Firstly, a solution of the resist composition is applied to a supporting member (e.g., silicon wafer) by spin coating or the like, followed by drying to form a photosensitive layer. Then, the photosensitive layer is exposed to an excimer laser light from an exposure apparatus through a desired mask pattern, followed by heating. Then, a 6 development treatment is conducted by using, for example, an alkali aqueous solution such as 0.1–10 wt % tetramethylammonium hydroxide aqueous solution, thereby obtaining a resist pattern conforming to the mask pattern.

According to need, it is optional to add a miscible additive to the polymer. Examples of such additive are additional resins, quencher, plasticizer, stabilizer, coloring agent, surfactant, tackifier, leveling agent, deforming agent, compatibility enhancing agent, adhesion enhancing agent, and antioxidant.

The following nonlimitative examples are illustrative of the present invention.

EXAMPLE 1

Synthesis of 2-(5-bicyclo[2,2,1]-2,5-heptadienyl)-1,1,1-trifluoro-2-(trifluoromethyl)$_2$-propanol (3)

This target product (3) was synthesized by the following steps (a) and (b), as shown by the following reaction formulas.

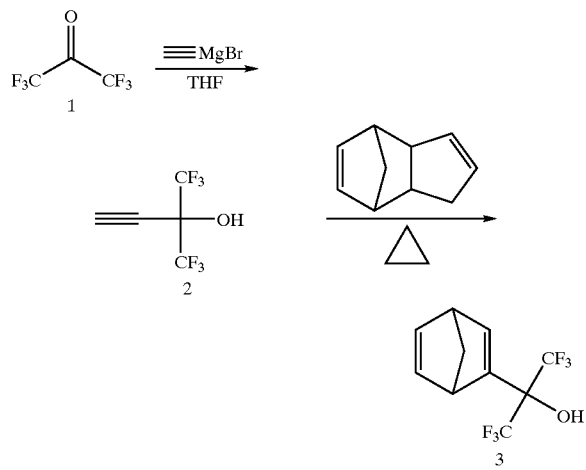

Step (a) synthesis of 1,1,1-trifluoro-2-(trifluoromethyl)-3-butyne-2-ol (2)

Under nitrogen gas flow, 2-liter four-necked flask was charged with 1.6 liter of a tetrahydrofuran solution (Grignard reagent solution) containing 0.5 M (molar concentration) of ethynylmagnesium bromide (Grignard reagent), and then the inside temperature was adjusted to 4° C. with an iced water bath. Then, the nitrogen gas flow was stopped, and a nitrogen-containing balloon was attached to the flask. Then, 132.8 g of hexafluoroacetone (1) were introduced, while the Grignard reagent solution was stirred. After stirring for 1 hr, 600 mL of 2N hydrochloric acid were gradually added. Then, an organic matter was extracted with tetrahydrofuran, and the resulting organic layer was washed two times with water and then one time with saturated brine, followed by drying with magnesium sulfate. The solvent was distilled off under reduced pressure, thereby obtaining 149.9 g of a distillate at 44° C. under 35 mmHg. This product was found by gas chromatography-mass spectrometry (GC-MAS) and nuclear magnetic resonance analysis (NMR) to be a complex of 1,1,1-trifluoro-2-(trifluoromethyl)-3-butyne-2-ol (2) (of one part) and tetrahydrofuran (of one part). The yield was 71%, based on hexafluoroacetone (1).

Step (b) synthesis of 2-(5-bicyclo[2,2,1]-2,5-heptadienyl)-1,1,1-trifluoro-2(trifluoromethyl)-2-propanol (3)

A 150 mL stainless steel (SUS) reaction tube was charged with 65.0 g of the product of the step (a) and 16.5 g of dicyclopentadiene. The reaction tube was sealed, followed by heating to 150° C. and stirring for 60 hr. After the reaction, the reaction tube was cooled down to lower the internal pressure. The content of the reaction tube was taken out, followed by a vacuum distillation, thereby obtaining 43.6 g of a distillate at 69–70° C. under 36 mmHg. This product w is found by NMR to be 2-(5-bicyclo[2,2,1]-2,5-heptadienyl)-1,1,1-trifluoro-2-(trifluoromethyl)-2-propanol (a). The yield was 68%, based on the product of the step (a).

NMR data of the product were as follows.
$^1$H-NMR (CDCl$_3$, TMS standard) δ: 7.07 (1H, d, J=3.2 Hz), 6.84(1H, dd, J=5.2 Hz, 3.2 Hz), 6.75 (1H, dd, J=5.2 Hz, 3.2 Hz), 3.78 (1H, br-s), 2.11 (1H, ddd, J=6.0 Hz, 1.6 Hz, 1.6 Hz), 2.05 (1H, ddd, J=6.0 Hz, 1.6 Hz, 1.6 Hz) $^{19}$F-NMR (CDCl$_3$, CFCl$_3$ standard) δ:-76.0(3SF, q, J=9.0 Hz),-76.3 (3F, q, J=9.0 Hz)

EXAMPLE 2

Synthesis of 2,3-bis(1,1,1,3,3,3-hexafluoro-2-hydroxyisopropyl) bicyclo[2.2.1]hepta-2,5-diene (5)

This target product (5) was synthesized by the following steps (a) and (b), as shown by the following reaction formulas.

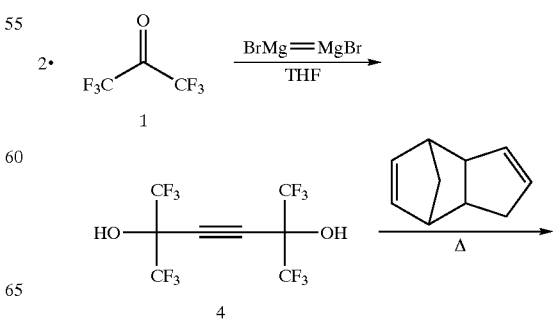

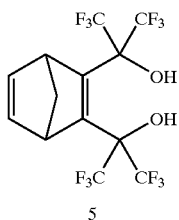

Step (a) synthesis of 2,5-bis(trifluoromethyl) 1,1,1, 6,6,6-hexafluoro 3-hexyne-2,5 diol (0.4)

A 5-liter flask (equipped with a reflux condenser, a thermometer, a dropping funnel, and a stirrer) was charged with 61 g of magnesium and 100 ml of tetrahydrofuran, and stirring was started while the inside of the reactor (flask) was made to have a nitrogen atmosphere. Then, a solution (prepared by dissolving 276 g of bromoethane in 2,900 ml of tetrahydrofuran (THF)) was added dropwise from the dropping funnel in a manner to adjust the reaction temperature to a range of 30° C. to 50° C. by regulating the rate of the addition of this solution. After the addition, stirring was continued at room temperature for 1 hr. Then, 31 g of acetylene gas were gradually bubbled into the reaction solution from a gas introducing tube, while an outlet of the gas introducing tube was immersed in the reaction solution. After the bubbling, stirring was continued at room temperature for 1 hr. Then, 400 g of hexafluoroacetone were bubbled in to the reaction solution from the gas introducing tube. After the bubbling, stirring was continued at room temperature for 12 hr.

After the reaction, the reaction solution was poured into 2 liters of iced water. Then, 2N hydrochloric acid was added to make the solution acid. The resulting organic phase was separated, followed by washing with water, then concentration and then vacuum distillation, thereby obtaining 364 g of a distillate (boiling point: 41° C./mmHg). This product was found by GC-MAS and NMR to be a complex of 2,5-bis (trifluoromethyl) 1,1,1,6,6,6-hexafluoro-3-hexyne 2,5-diol (4) (one part) and tetrahydrofuran (one part). The yield was 70%, based on hexafluoroacetone (1).

Step (b) synthesis of 2,3-bis(1,1,1,8,3,83-hexafluoro-2-hydroxyisopropyl) bicyclo[2.2.1]hepta-2,5-diene (0.5)

A 160 mL stainless steel (SUS) reaction tube was charged with 143.6 g of the product of the step (a) and 22.7 g of dicyclopentadiene. The reaction tube was sealed, followed by heating to 170° C. and stirring for 42 hr. After the reaction, the reaction tube was cooled down to lower the internal pressure. The content of the reaction tube was taken out, followed by a vacuum distillation to remove low-boiling point substances. The resulting crude crystals (as residue) were subjected to a vacuum sublimation purification under heating, thereby obtaining 80.8 g of white crystals. This product was found by NMR to be 2,3-bis(1,1,1,3,3,3-hexafluoro-2-hydroxyisopropyl)bicyclo[2.2.1]hepta-2,5-diene. The yield was 58%, based on the product of the step (a).

NMR data of the product were as follows.
$^1$H-NMR (CDCl$_3$, TMS standard) δ: 6.80 (2H, a), 6.41 (2H, br-s), 4.01 (2H, s), 2.11 (1H, d, J=6.4 Hz), 1.92 (1H, d, J=6.41 Hz) $^{19}$F-NMR (CDCl$_3$, CFCl$_3$ standard) δ:–74.3 (3F, q, J=9.0 Hz),–74.7 (3F, q, J=9.0 Hz)

EXAMPLE 3

An alcohol (6) was prepared from 2-(5-bicyclo[2,2,1]-2, 5-heptadienyl)-1,1,1-trifluoro-2-(trifluoromethyl)-2-propanol (3) by the following procedures, as shown by the following reaction formula.

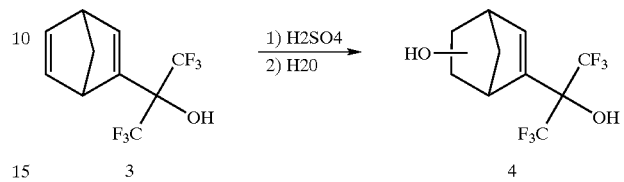

A 300 ml flask (equipped with a reflux condenser, a dropping funnel, a thermometer, and a stirrer) was charged with 46 g of sulfuric acid under nitrogen gas flow, and the flask bottom was cooled down in an iced water bath. Then, 40 g of 2-(5-bicyclo[2,2,1]-2,5-heptadienyl)-1,1,1-trifluoro-2-(trifluoromethyl)-2 propanol (3) were added dropwise from the dropping funnel in a manner that the temperature of the reaction solution did not exceed 50° C. After the addition, stirring was further continued at room temperature for 3 hr. Then, the flask bottom was cooled down in an iced water bath, and 150 nm of water were added dropwise from the dropping funnel. After the addition, the temperature of the reaction solution was increased using an oil bath in place of the iced water bath, and stirring was conducted at reflux temperature for 1 hr.

After the reaction, the reaction solution was poured into 1,000 ml of iced water, followed by extraction with 300 ml of diethyl ether. The resulting organic phase was washed with water, followed by drying with magnesium sulfate. The obtained solution was concentrated under reduced pressure, followed by vacuum distillation to obtain 33 g of a distillate of at a temperature of 85 to 90° C. under 1 mmHg. This product was found by GC-MAS and NMR to be a mixture of three isomers of the alcohol (6).

NMR data of the product were as follows.

$^1$H-NMR (CDCl$_3$, TMS standard) δ: 6.59 (1H, d, J=2.8 Hz), 6.52 (1H, d, J=3.2 Hz), 6.89 (1H, d, J=3.2 Hz), 5.14 (1H, s), 4.64 (1H, m), 4.06 (1H, d, J=6.4 Hz), 3.97 (1H, d, J=6.0 Hz), 3.87 (1H, s), 8.71 (1H, s), 3.08–3.14 (3H, m), 3.00 (1H, r), 2.96 (1H, m), 2.87 (1H, m), 2.13–2.21 (1H, m), 1.64–1.93 (8H, m), 1.35–1.45 (2 H, m), 1.01–1.07 (1H, m) $^{19}$F-NMR (CDCl$_3$, CFCl$_3$ standard) δ:–75.3 (3F, q, J=9.7 Hz),–76.4–– 76.2 (9F, m),–76.6(3F, q, J=9.7 Hz), –76.8 (3F, q, J=0.85 Hz)

EXAMPLE 4

An alcohol (7) was prepared from 2,3-bis(1,1,1,3,3,3-hexafluoro-2-hydroxyisopropyl)bicyclo[2.2]hepta-2,5-diene (5) by the following procedures, as shown by the following reaction formula.

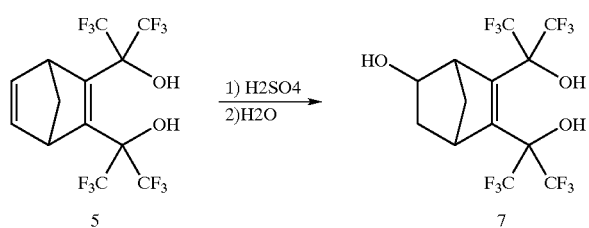

A 300 ml flask (equipped with a reflux condenser, a dropping funnel, a thermometer, and a stirrer) was charged with 50 g of 2,3-bis(1,1,1,3,3,3-hexafluoro-2-hydroxyisopropyl)bicyclo[2.2.1]hepta-2,5-diene (5) under nitrogen gas flow, and the flask bottom was cooled down in an iced water bath. Then, 50 g of sulfuric acid were added dropwise from the dropping funnel in a manner that the temperature of the reaction solution did not exceed 50° C. After the addition, stirring was further continued at room temperature for 3 hr. Then, the flask bottom was cooled down in an iced water bath, and 150 ml of water were added dropwise from the dropping funnel. After the addition, the temperature of the reaction solution was increased using an oil bath in place of the iced water bath, and stirring was conducted at reflux temperature for 1 hr.

After the reaction, the reaction solution was poured into 1,000 ml of iced water, followed by extraction with 300 ml of diethyl ether. The resulting organic phase was washed with water, followed by drying with magnesium sulfate. The obtained solution was concentrated under reduced pressure, followed by purification using silica gel chromatography (hexane:diethyl ether=50:50–30:70), thereby obtaining 34 g of a product. This product was found by GC-MAS and NMR to be the alcohol (7).

NMR data of the product were as follows.
$^1$H-NMR (acetone deuteride, TMS standard) δ: 9.30 (2H, br-s), 4.38 (1H, br-s), 4.12 (1H, 8), 3.26 (1H, s), 3.16 (1H, s), 1.85–1.97 (2H, m), 1.77–1.79 (1H, m), 1.50–1.55 (1H, m) $^{19}$F-NMR (acetone deuteride, CFCl$_3$ standard) δ:–72.7 (3F, q, J=9.7 Hz), –73.1 (3F, q, J=9.7 Hz), –73.2 (6F, m)

EXAMPLE 5

A vinyl ether (8) was prepared from an alcohol (6) by the following procedures, as shown by the following reaction formula.

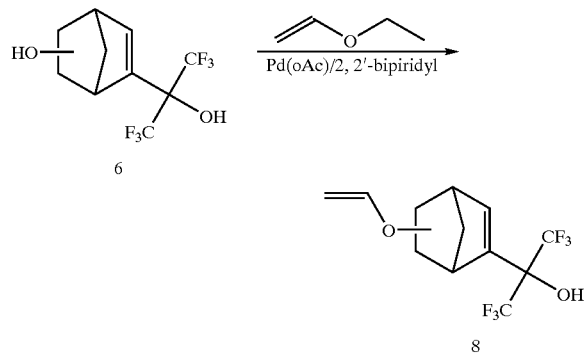

A 30 ml flask (equipped with a reflux condenser, a dropping funnel, a thermometer, and a stirrer) was charged with 1.5 g of the alcohol (6) under nitrogen gas flow, and the flask bottom was cooled down in an iced water bath. Then, the flask was further charged with 66.3 mg of palladium acetate, 0.47 g of 2,2'-bipiridyl, and 7.8 g of ethyl vinyl ether, followed by stirring at room temperature for 3 hr.

After the reaction, the reaction solution was poured into 100 ml of iced water, followed by extraction with 100 ml of diethyl ether. The resulting Organic phase was washed with water, followed by drying with magnesium sulfate. The obtained solution was concentrated under reduced pressure, followed by purification using silica gel chromatography (hexane:diethyl ether 90:10–75:25), thereby obtaining 1.1 g of a product. This product was found by NMR to be a mixture of three kinds of isomers of the vinyl ether (8).

NMR data of the product were as follows.
$^1$H-NMR (CDCls, TMS standard) δ: 6.67 (1H, d, J=2.8 Hz), 6.47 (1H, d, J=3.2 Hz), 6.42 (1H, d, J=4.0 Hz), 6.38 (1H, dd, J=14.4 Hz and 6.8 Hz), 6.37 (1H, dd, J=14.4 Hz and 6.8 Hz), 6.31 (1H, dd, J=14.4 Hz and 6.8 Hz), 4.27 (1H, dd, J=14.4 Hz and 1.6 Hz), 4.20 (1H, dd, J=14.4 Hz and 2.0H$_2$), 4.19 (1H, dd, J=14.4 Hz and 1.6 Hz), 4.08 (1H, d, J=6.4 Hz), 4.05 (1H, dd, J=6.8 Hz and 2.0 Hz), 4.04 (1H, dd, J=6.8 Hz and 1.6 Hz), 4.02 (1H, dd, J=6.8 Hz and 1.6 Hz), 3.98 (1H, d, J=6.0 Hz), 2.97–3.33 (6H, m), 1.19–2.18 (12H, m)
$^{19}$F-NMR (CDCL$_3$, CFCl$_3$ standard) δ:–75.9 (3F, q, J=9.6 Hz),–76.2—76.5 (9F, m),–76.7 (3F, q, J-9.6 Hz)

EXAMPLE 6

An α-trifluoromethylacrylic ester (9) was prepared from an alcohol by the following procedures, as shown by the following reaction formula.

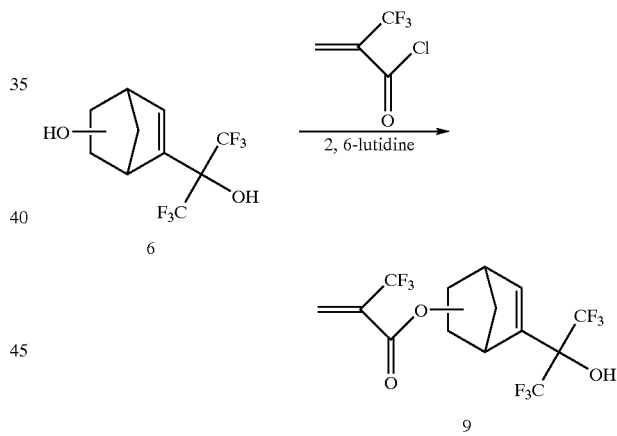

A 100 ml flask (equipped with a reflux condenser, a dropping funnel, a thermometer, and a stirrer) was charged with 2.0 g of the alcohol (6) under nitrogen gas flow, and the flask bottom was cooled down in an iced water bath. Then, the flask was further charged with 1.5 g of α-trifluoromethylacrylic chloride, 11.0 g of 2,6-lutidine, and 20 ml of toluene, followed by a stirring for 3 hr and a further stirring at room temperature for 1 hr.

After the reaction, iced water was added, followed by adding 200 ml of diethyl ether for extraction. The resulting organic phase was washed with water, followed by drying with magnesium sulfate. The obtained solution was concentrated under reduced pressure, followed by purifcation using silica gel chromatography (hexane: diethyl ether=90:10–75:25), thereby obtaining 1.5 g of a product. This product was found by NMR to be a mixture of three kinds of isomers of the α-trifluoromethylacrylic ester NMR data of the product were as follows.

$^1$H-NMR (CDCl$_3$, TMS standard) δ: 6.73 (2H, m), 6.71 (1H, d, J=3.2 Hz), 6.61 (1H, m), 6.46 (1H, d, J-3.6 Hz), 6.44 (3H, m), 6.39 (1H, m), 5.56 (1H, m), 4.96 (1H, d, J=7.2 Hz), 4.90 (1H, d, J=6.8 Hz), 8.05–3.42 (6H, m), 1.22–2.35 (12H, m)

$^{19}$F-NMR (CDCls, CFCl$_3$ standard) δ: −65.99 (3F, 8), −66.01(3F, s),−76.20−−76.40 (12F, m),−76.45 (3F, q, J=9.6 Hz),−76.79 (3F, q, J=9.6 Hz)

EXAMPLE 7

A methacrylic ester (10) was prepared from an alcohol (7) by the following procedures, as shown by the following reaction formula.

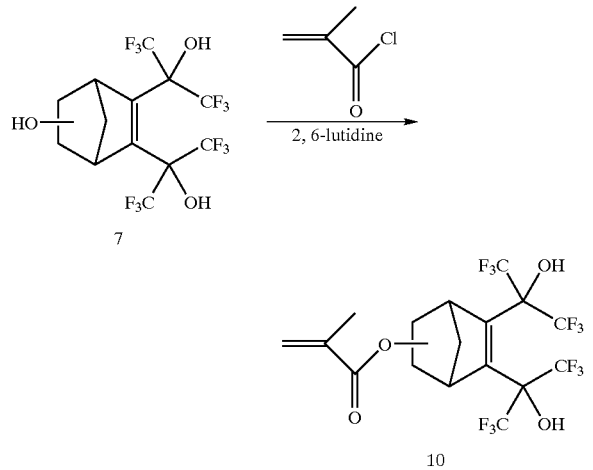

A 300 ml flask (equipped with a reflux condenser, a dropping funnel, a thermometer, and a stirrer) was charged with 10.5 g of the alcohol (U) and 120 ml of toluene under nitrogen gas flow, and the flask bottom was cooled down in an iced water bath. Then, the flask was further charged with 2.7 g of methacrylic chloride. After that, 5.1 g of 2,6-lutidine were gradually added dropwise, followed by a stirring for 3 hr and then a further stirring at room temperature for 1 hr.

After the reaction, the reaction solution was poured into 1,000 ml of iced water, followed by adding 300 ml of diethyl ether for extraction. The resulting organic phase was washed with water, followed by drying with magnesium sulfate. The obtained solution was concentrated under reduced pressure, followed by purification using silica gel chromatography (hexane:diethyl ether=75:25), thereby obta g 6.2 g of a product. This product was found by NMR to be the methacrylic ester (10).

NMR data of the product were as follows.

$^1$H-NMR (acetone deuteride, TMS standard) δ: 6.09 (1H, br-s), 6.59 (1H, br-s), 5.00 (1H, d, J=6.8 Hz), 3.39 (1H, br-s), 3.33 (1H, br-s), 2.14–2.06 (1H, m), 1.99–1.80 (2H, m), 1.94 (3H, 9), 1.64 (1H, dt, J=12.8 Hz and 2.8 Hz) $^{19}$F-NMR (acetone deuteride, CFC$_3$ standard) δ:−73.8 (3F, q, J=9.6 HZ, −73.9−−74.4(6F, m),−74.5(3F, q, J=9.6 Hz)

EXAMPLE 8

An α-trifluoromethylacrylic ester (11) was prepared from an alcohol (7) by the following procedures, as shown by the following reaction formula.

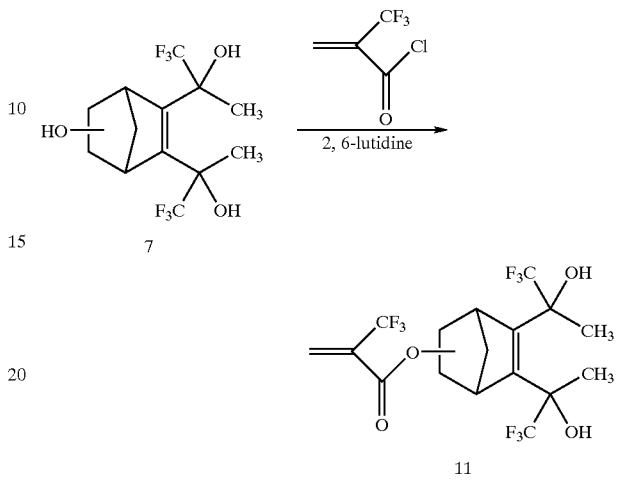

A 300 ml flask (equipped with a reflux condenser, a dropping funnel, a thermometer, and a stirrer) was charged with log of the alcohol (7) and 50 ml of toluene under nitrogen gas flow, and the flask bottom was cooled down in an iced water bath. Then, the flask was further charged with 4.6 g of α-trifluoromethylacrylic chloride. After that, 3.6 g of 2,6-lutidine were gradually added dropwise with a stirring for 3 hr, followed by a further stirring at room temperature for 1 hr.

After the reaction, the reaction solution was poured into 1,000 ml of iced water, followed by adding 300 ml of diethyl ether for extraction. The resulting organic phase was washed with water, followed by drying with magnesium sulfate. The obtained solution was concentrated under reduced pressure, followed by purification using silica gel chromatography (hexane:diethyl ether=75:25), thereby obtaining 7.0 g of a product. This product was found by NMR to be the α-trifluoromethylacrylic ester (11).

NMR data of the product were as follows.

$^1$H-NMR (acetone deuteride, TMS standard) δ: 6.89 (1H, br-s), 6.66 (1H, br-s), 5.14 (1H, d, J=7.2 Hz), 3.47 (1H, br-s), 3.41 (1H, br-s), 2.12–2.08 (2H, m), 1.94–1.87 (1H, m), 1.84 (1H, dt, J-13.6 Hz and 2.8 Hz) $^{19}$F-NMR (acetone deuteride, CFCl$_3$ standard) δ: −64.9(3F, 6),−72.6(3F, q, J=9.6 Hz),−72.8−−73.2(6F, m),−73.3(3F, q, J=9.6 Hz

EXAMPLE 9

A polymer 1 was prepared from the compound (10) by the following procedures, as shown by the following reaction formula.

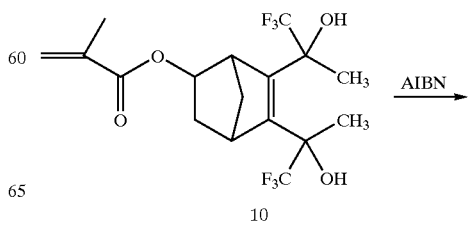

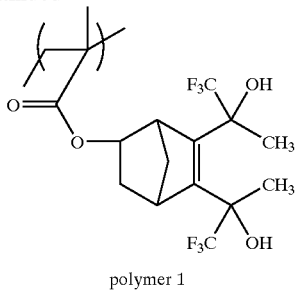

polymer 1

A flask (equipped with a reflux condenser and a stirrer) was charged with 5.0 g of the compound (I), 2 g of n-butyl acetate, and 75 mg of azobisbutyronitrile (AIBN) under nitrogen gas flow, followed by heating in an oil bath of 60° C. with stirring for 20 hr.

After the reaction, 200 ml of n-hexane were added, followed by stirring. The resulting precipitate was taken out by filtration, followed by vacuum drying at 50° C. for 18 hr, thereby obtaining 3.90 g of a product as a white solid. This product was identified by NMR as the polymer 1.

The molecular weights (Mw: weight-average molecular weight; Mn: number-average molecular weight) of the polymer 1 were determined by gel permeation chromatography (GPC) using polystyrene as standard. With this, Mw was 29,500, and the ratio of Mw/Mn was 1.5.

EXAMPLE 10

A polymer 2 was prepared from the polymer 1 through methoxymethylation of hexafluorocarbinol groups of the polymer 1 by the following procedures, as shown by the following reaction formula.

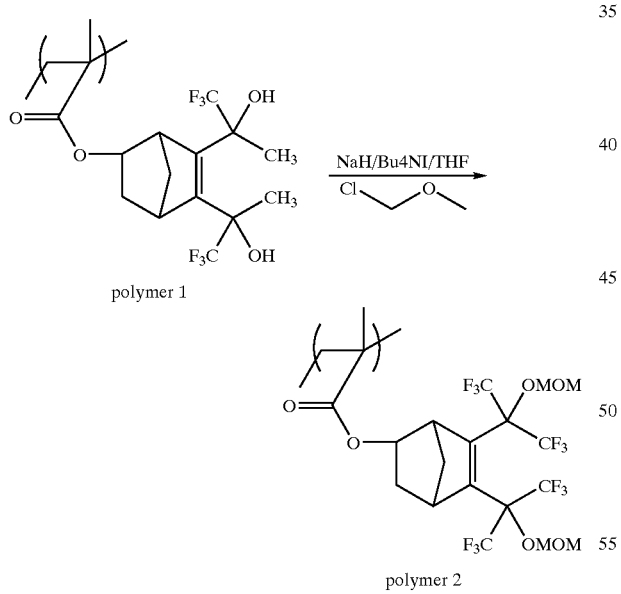

A flask (equipped with a reflux condenser and a stirrer) was charged with 1 g of the polymer 1,20 g of tetrahydrofuran, and 100 mg of tetrabutylammonium iodide under nitrogen gas flow with stirring, and the flask bottom was cooled down in at iced water bath. Then, the flask was further charged with 0.13 g of NaOH, followed by stirring for 15 min.

After the reaction, 100 ml of water were added, followed by stirring. The resulting precipitate was taken out by filtration, followed by vacuum drying at 50° C. for 18 hr, thereby obtaining 0.88 g of a product as a white solid. This product was identified by NMR as the polymer 2. The molecular weights of the polymer 2 were determined as in Example 9. With this, Mw was 29,700, and the ratio of Mw/Mn was 1.5.

EXAMPLE 11

A copolymer of the compound (10), methyladamantylmethacrylate, and maleic anhydride (see the following formulas) was prepared by the following procedures.

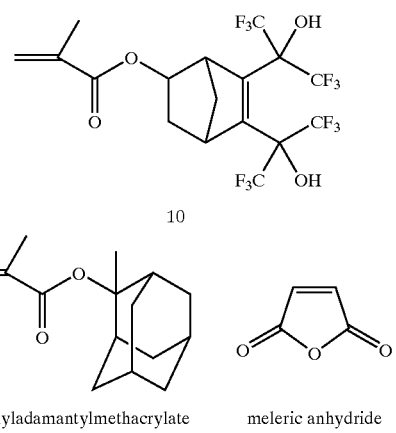

methyladamantylmethacrylate    meleric anhydride

A flask (equipped with a reflux condenser and a stirrer) was charged with 3 g of the compound (10), 1 g of methyladamantylmethacrylate, 1 g of maleic anhydride, 2 g of n-butyl acetate, and 75 mg of AIBN under nitrogen gas flow, followed by heating in an oil bath of 60° C. with stirring for 20 hr.

After the reaction, 200 ml of n-hexane were added, followed by stirring. The resulting precipitate was taken out by filtration, followed by vacuum drying at 50° C. for 18 hr, thereby obtaining 3.29 g of a product as a white solid. This product was identified by NMR as a polymer 3. The molecular weights of the polymer 3 were determined as in Example 9. With this, Mw was 11,100, and the ratio of Mw/Mn was 1.4.

EXAMPLE 12

A copolymer of the compound (8) and tbutyl α-trifluoromethyl acrylate (see the following formulas) was prepared by the following procedures.

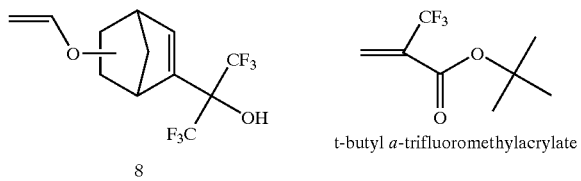

8    t-butyl a-trifluoromethylacrylate

A flask (equipped with a reflux condenser and a stirrer) was charged with 3 g of the compound (8), 2 g of tbutyl c-trifluoromethyl-acrylate, 2 g of n-butyl acetate, and 56 mg of AIBN under nitrogen gas flow, followed by heating in an oil bath of 60° C. with stirring for 20 hr.

After the reaction, 200 ml of n-hexane were added, followed by stirring. The resulting precipitate was taken out by filtration, followed by vacuum drying at 50° C. for 18 hr, thereby obtaining 3.11 g of a product as a white solid. This product was identified by NMR as a polymer 4. The molecular weights of the polymer 4 were determined as in Example 9. With this, Mw was 61,900, and the ratio of Mw/Mn was 1.6.

EXAMPLE 13

A copolymer of the compound (9) and BTHB-NB-MOM (see the following formulas) was prepared by the following procedures.

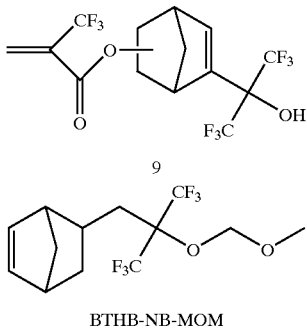

BTHB-NB-MOM

A flask (equipped with a reflux condenser and a stirrer) was charged with 3 g of the compound (9), 2 g of BTHB-NB-MOM, 2 g of n-butyl acetate, and 75 mg of AIBN, followed by heating in an oil bath of 60° C. with stirring for 20 hr.

After the reaction, 200 ml of n-hexane were added, followed by stirring. The resulting precipitate was taken out by filtration, followed by vacuum drying at 50° C. for 18 hr, thereby obtaining 2.21 g of a product as a white solid. This product was identified by NMR as a polymer 5. The molecular weights of the polymer 5 were determined as in Example 9. With this, Mw was 32,000, and the ratio of Mw/Mn was 1.5.

EXAMPLE 14

The polymers obtained in Examples 1013 were dissolved in propylene glycol monomethyl acetate to have a solid matter concentration of 14%. Then, an acid generator, triphenylsulfonium triflate (TPS105) made by Midori Kagaku Co., Ltd., was dissolved in an amount of 2 parts by weight per 100 parts by weight of each polymer, thereby preparing resist solutions of Examples 10–13. These resist solutions were applied to substrates by spin coating. The resulting resist films were found to have light transmittances of 68%, 21%, 38% and 55% in Examples 10–13 respectively at a wavelength of 157 nm and at a film thickness of 100 nm, showing high transparency in vacuum ultraviolet wavelength region.

Then, the above resist solutions were filtered with a membrane filer (pore diameter: 0.2 micrometers). The resulting resist solutions were applied to silicon wafers by spin coating to form resist films each having a thickness of 260 nm. Then, the resist films were subjected to a preliminary baking at 110° C., followed by exposure to a 248 nm ultraviolet ray through a photomask and then by a post exposure baking at 120 w. Then, the resist films were developed at 23° C. for 1 minute using 2.38 wt% tetramethylammonium hydroxide aqueous solution to form resist patterns. Each resist pattern had a high resolution and no development defects.

The entire disclosure of Japanese Patent Application Nos. 2003-043496 (filed on Feb. 21, 2003) and 2003-135228 (filed on May 14, 2008), which are basic Japanese patent applications of the present application, including specification, claims and summary, is incorporated herein by reference in its entirety.

What is claimed is:

1. A fluorine-containing cyclic compound represented by the formula 1:

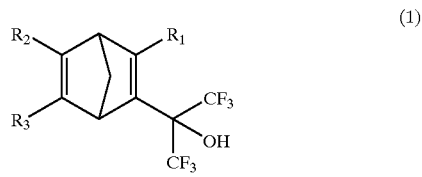

wherein each of $R_1$, $R_2$ and $R_3$ independently represents a hydrogen, alkyl group, fluorine, fluoroalkyl group or hexafluorocarbinol group, wherein at least one of the hexafluorocarbinol groups may partly or totally be protected with a protecting group, and wherein the protecting group is (a) a straight-chain, branched or cyclic hydrocarbon group having a carbon atom number of 1–25 or (b) an aromatic hydrocarbon group and optionally contains a fluorine atom, oxygen atom, nitrogen atom or carbonyl bond.

2. A fluorine-containing cyclic compound represented by the formula 2

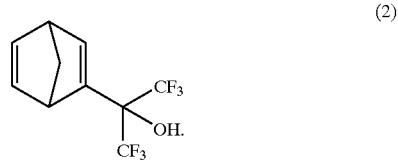

3. A fluorine-containing cyclic compound represented by the formula 3

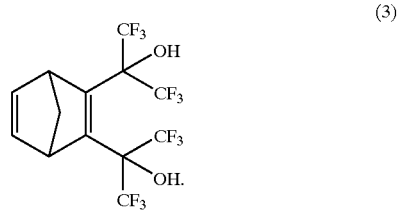

4. A fluorine-containing cyclic compound derived from the fluorine-containing cyclic compound according to claim 1 and represented by the formula 4 or 5:

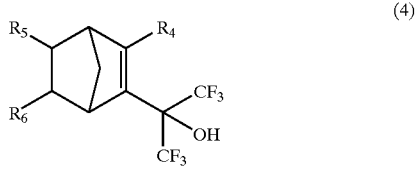

-continued

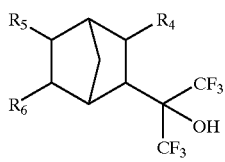
(5)

wherein at least one of $R_4$, $R_5$ and $R_6$ represents a hydroxyl group, and the remaining group of $R_4$, $R_5$ and $R_6$ other than the hydroxyl group represents a hydrogen, alkyl group, fluorine, fluoroalkyl group, or hexafluorocarbinol group, wherein at least one of the hexafluorocarbinol groups of the formula 4 or 5 may partly or totally be protected with a protecting group, and wherein the protecting group is (a) a straight-chain, branched or cyclic hydrocarbon group having a carbon atom number of 1–25 or (b) an aromatic hydrocarbon group and optionally contains a fluorine atom, oxygen atom, nitrogen atom or carbonyl bond.

5. A fluorine-containing cyclic compound represented by the formula 6 or 7

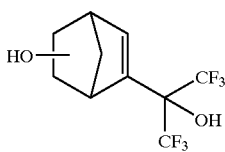
(6)

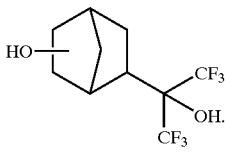
(7)

6. A fluorine-containing cyclic compound represented by the formula 8 or 9

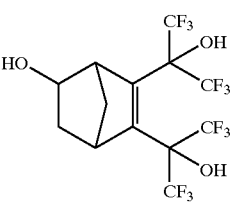
(8)

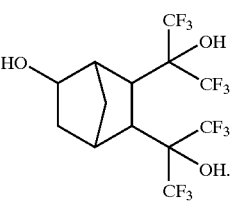
(9)

7. A fluorine-containing polymerizable monomer derived from the fluorine-containing cyclic compound according to claim 4 and represented by the formula 10 or 11:

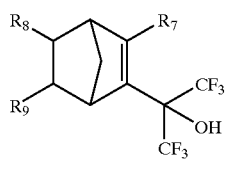
(10)

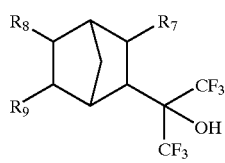
(11)

wherein one of $R_7$, $R_8$ and $R_9$ in the formula 10 or 11 is a polymerizable group, and the remaining group of $R_7$, $R_8$ and $R_9$ other than the polymerizable group represents a hydrogen, alkyl group, fluorine, fluoroalkyl group, or hexafluorocarbinol group, wherein at least one of the hexafluorocarbinol groups of the formula 10 or 11 may partly or totally be protected with a protecting group, wherein the protecting group is (a) a straight-chain, branched or cyclic hydrocarbon group having a carbon atom number of 1–20 or (b) an aromatic hydrocarbon group and optionally contains a fluorine atom, oxygen atom, nitrogen atom or carbonyl bond, and wherein the polymerizable group is represented by the formula 12:

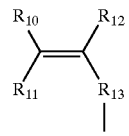
(12)

wherein each of $R_{10}$ to $R_{12}$ independently represents a hydrogen atom, fluorine atom, or a straight-chain, branched or cyclic alkyl or fluoroalkyl group having a carbon atom number of 1–25, and wherein $R_{13}$ a represents a single bond, a methylene group, a straight-chain, branched or cyclic fluoroalkylene group having a carbon atom number of 2–20, an oxygen atom, a sulfur atom, —(C=O)O—, or a dialkylsilylene group.

8. A fluorine-containing polymerizable monomer according to claim 7, which is an acrylic ester, methacrylic ester, α-trifluoromethylacrylic ester, vinyl ether, or allyl ether.

9. A fluorine-containing polymerizable monomer represented by the formula 13 or 14

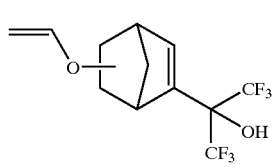
(13)

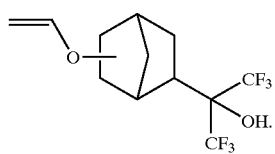

(14)

10. A fluorine-containing polymerizable monomer represented by the formula 15 or 16:

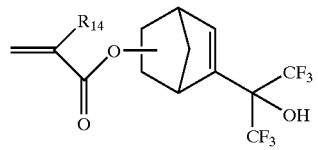

(15)

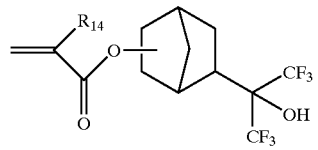

(16)

wherein $R_{14}$ of the formula 15 or 16 represents a hydrogen, methyl group or trifluoromethyl group.

11. A fluorine-containing polymerizable monomer represented by the formula 17 or 18:

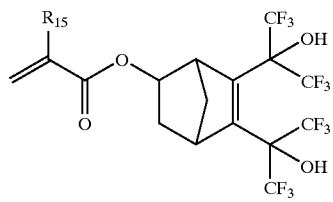

(17)

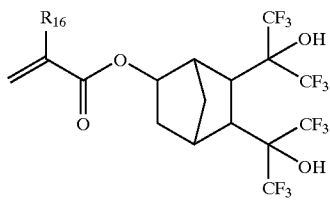

(18)

wherein $R_{15}$ of the formula 17 or 18 represents a hydrogen, methyl group or trifluoromethyl group.

12. A fluorine-containing cyclic compound according to claim 1, wherein at least one of the hexafluorocarbinol groups of the formula 1 is partly or totally protected with an acid-labile protecting group.

13. A fluorine-containing polymer prepared by a polymerization or copolymerization using the fluorine-containing cyclic compound according to claim 1.

14. A resist composition comprising a fluorine-containing polymer according to claim 13.

15. A process for making a resist pattern, comprising the sequential steps of:

(a) applying a resist composition according to claim 14 to a supporting member to form a photosensitive layer on the supporting member;

(b) exposing the photosensitive layer to a light through a masking pattern to form a first precursory layer;

(c) heating the first precursory layer into a second precursory layer; and (d) developing the second precursory layer into the resist pattern.

* * * * *